Figure 10:
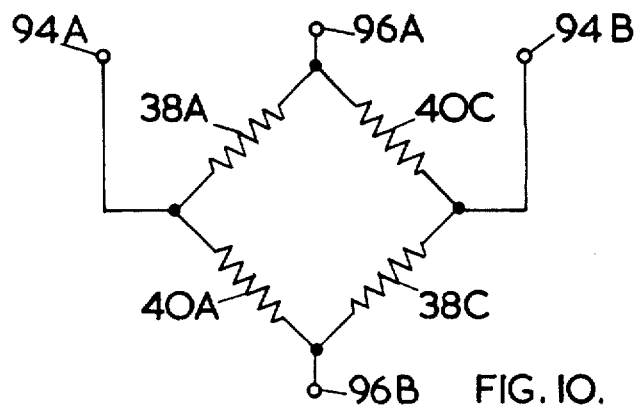

United States Patent [19]

Bingham

[11] 3,938,379

[45] Feb. 17, 1976

[54] ELECTROMECHANICAL TRANSDUCER

[75] Inventor: Rowland Hardy Bingham, Littlehampton, England

[73] Assignee: National Research Development Corporation, London, England

[22] Filed: Jan. 10, 1974

[21] Appl. No.: 432,394

[30] Foreign Application Priority Data

Jan. 12, 1973 United Kingdom............ 1674/73

[52] U.S. Cl............................................. 73/141 A
[51] Int. Cl.$^2$........................................ G01L 1/22
[58] Field of Search............. 73/88.5 R, 141 A, 143

[56] References Cited
UNITED STATES PATENTS

| | | |
|---|---|---|
| 2,440,706 | 5/1948 | Tint................ 73/141 A X |
| 2,795,134 | 6/1957 | Weber et al............ 73/141 A |
| 3,100,990 | 8/1963 | Dimeff................ 73/147 |
| 3,513,431 | 5/1970 | Kovacs............ 73/141 A X |
| 3,600,942 | 8/1971 | Brendel............ 73/141 A |

FOREIGN PATENTS OR APPLICATIONS 1,538,992  8/1968  France............ 73/88.5 R

*Primary Examiner*—Charles A. Ruehl
*Attorney, Agent, or Firm*—Cushman, Darby & Cushman

[57] ABSTRACT

A lightweight electromechanical transducer is described having a substantially cylindrical main body disposed around a longitudinal central axis. The main body is split into two end portions and a flexure element is provided between the end portions. Pillars join the flexure element to each of the end portions. Strain gauges are mounted on the flexure element.

22 Claims, 13 Drawing Figures

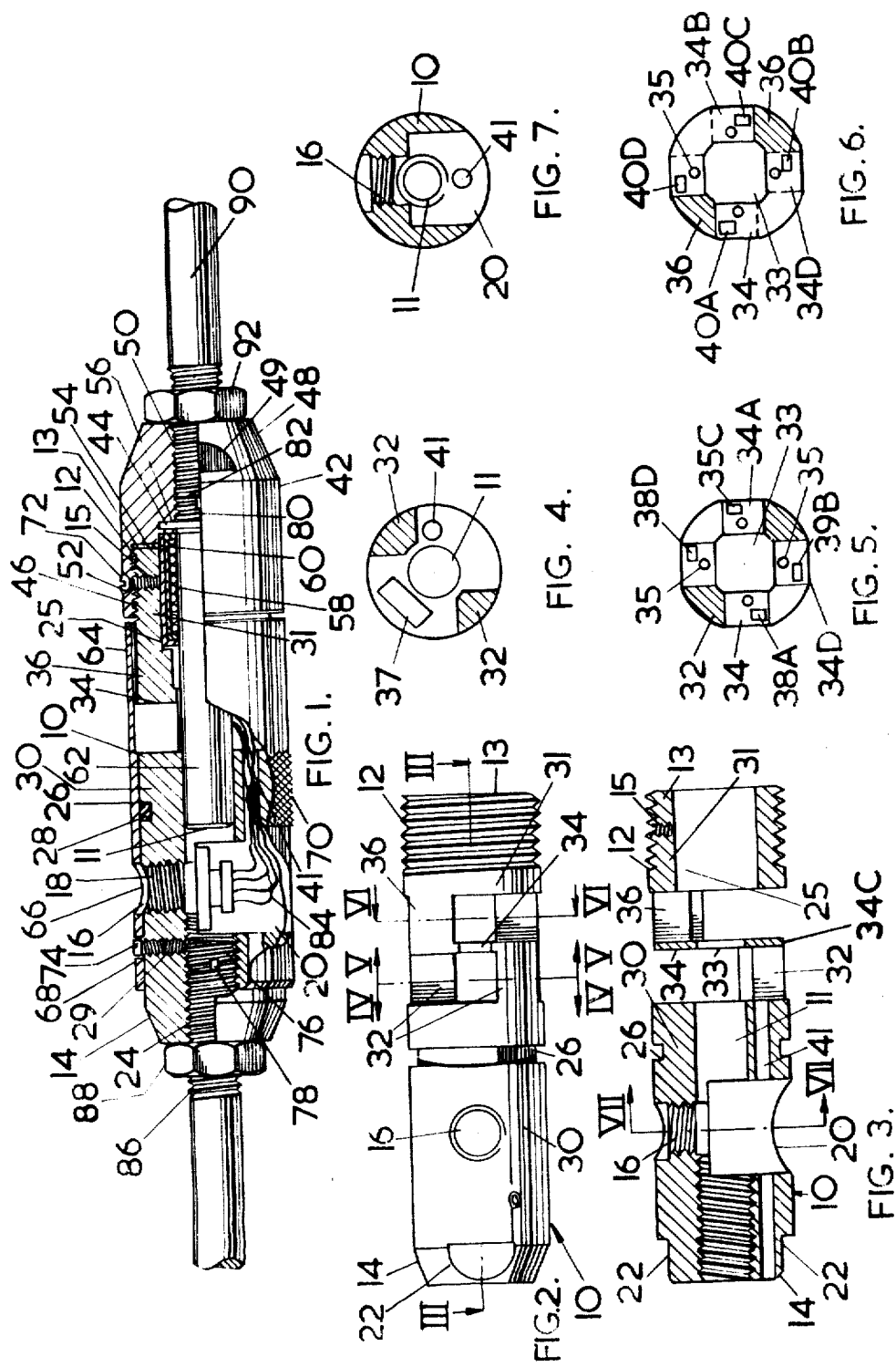

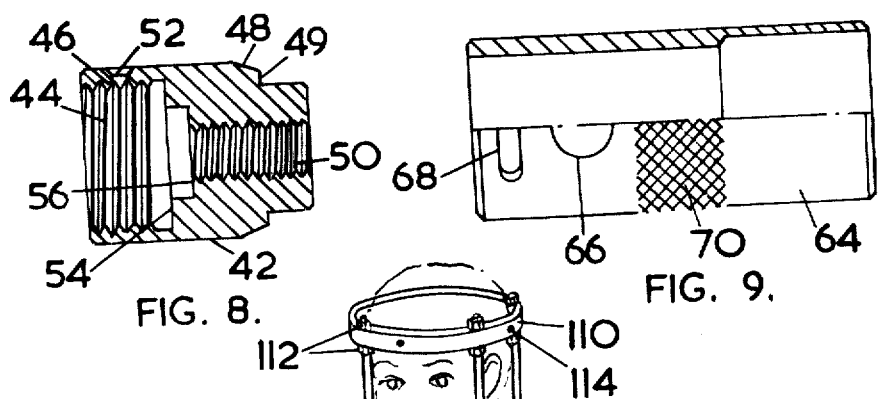
FIG. 8.
FIG. 9.
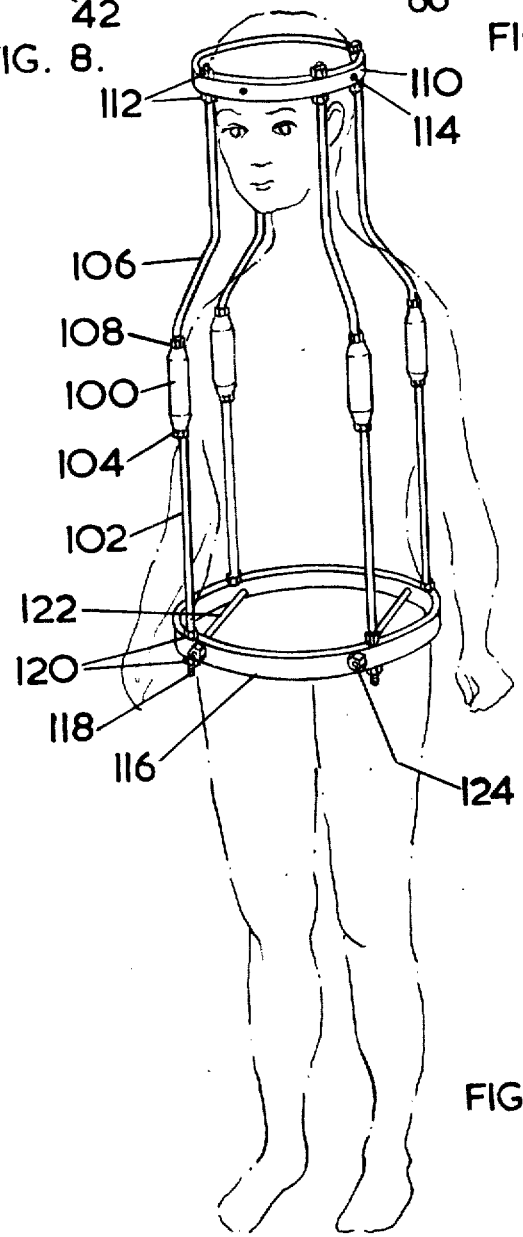
FIG. 13.

ELECTROMECHANICAL TRANSDUCER

This invention relates to electro-mechanical transducers. The invention particularly concerns a transducer for responding to stresses in rods, bars, and the like and providing an electrical output corresponding to the stress. While the invention has been developed with application to halo-pelvic traction in mind, it is by no means limited to this, the invention finds application in any field in which a compact comparatively likeweight robust transducer for measuring small stress variations is required.

Halo-Pelvic Traction is a new form of treatment in the field of orthopaedics whereby badly deformed spines of children are corrected by applying controlled forces between the pelvic girdle and the skull through four equi-spaced steel bars. No real accuracy in setting-up the apparatus or monitoring of the forces has hitherto been achieved. The loading in each bar must necessarily be uniform and is critical to the extent that excess traction can prove fatal. Once the load is applied it is held until, through the passage of time, the spine begins to straighten and a decay of the total force takes place. The characteristics of this decay are of paramount importance in the medical profession to determine spinal resistance and, indeed, as a guide to subsequent adjustment. A high degree of accuracy and stability is therefore required over a considerable period of time.

Attempts have been made to measure the stresses in the rods of such halo-pelvic traction equipment by bonding foil strain gauges directly to the bars of the equipment, however this has proved to be impracticable because of lack of rigidity, gauge vulnerability, and physical hazard to the patient from metal protrusions.

Load cells available for measuring stresses have not been suitable for this application because of their great weight and size, and the face that they are insensitive to small changes of stress.

According to the present invention there is provided an electromechanical transducer including a substantially cylindrical main body disposed around a longitudinal central axis, the main body comprising two end portions and a flexure element disposed in a plane normal to the central axis, the flexure element comprising a pair of parallel surfaces connected by a rim and being joined to one of said end portions by at least one first pillar extending in a direction parallel to the longitudinal central axis of the main body and being joined to the other end portions by at least one second pillar extending in a direction parallel to the longitudinal central axis of the main body, and at least one strain gauge mounted on said flexure element. It has been found that an electromechanical transducer in accordance with the present invention can be constructed with the minimum of weight and is extremely sensitive to small changes of applied loading. It is in consequence extremely well suited in the application to halo-pelvic traction described in the preceeding paragraphs.

Preferably in accordance with the invention an electromechanical transducer includes a substantially cylindrical main body disposed around a central longitudinal axis, the main body comprising two end portions and a flexure element disposed in a plane normal to the central axis, the flexure element comprising a pair of parallel surfaces connected by a rim and being joined to one of the said end portions by a pair of diametrically opposed first pillars extending in a direction parallel to the longitudinal central axis of the main body and to the other of said end portions by at least a pair of diametrically opposed second pillars, said second pillars being disposed orthogonally of the first pillars, and at least two pairs of strain gauges, first gauges of each pair being mounted on one of the parallel surfaces of the flexure element and the second gauges of each pair being mounted on the other parallel surface of the flexure element opposite the first strain gauge of the pair.

The flexure element may preferably be shaped so as to act as a plurality of guided cantilevers. In this form an extremely sensitive response is obtained.

One of the problems in using an arrangement of strain gauges having, say, two pairs of strain gauges mounted on for example diametrically opposed guided cantilivers and described in the preceding paragraphs is that there is a limited amount of interaction between torsional and transverse loading. To overcome this problem a electromechanical transducer in accordance with the invention and characterized in that the flexure element is arranged as four guided cantilivers is provided with eight strain gauges arranged in four pairs, one pair mounted on each of the guided cantilivers and in the corresponding position to each of the other pairs.

For greatest response the strain gauges are preferably mounted at a position midway between the root and the point of inflection of each guided cantilever.

Preferably an electromechanical transducer in accordance with the present invention includes an axial bore.

It is desirable in a electromechanical transducer as described to prevent or reduce bending of the transducer. To overcome this the present invention, in one aspect thereof, includes a rod mounted with the axial base described in the preceding paragraph. In a further feature the rod is journalled in a ball bushing.

In a further feature of the invention the axial base as described above is threaded towards either end. The treads may engage threaded rods of, for example, a halo-pelvic traction equipment, alternatively or in addition, threaded plugs may engage the threads in the axial base to prevent over screwing of the rods damaging the interior wiring of the device or prevent foreign bodies being pushed down the axial bore damaging the interior wiring.

A further important, optional feature, is the provision of an end cap. The end cap may in addition retain the ball bushing in position.

To permit the engagement and disengagement of an external plug to, for example, metering equipment, the main body may be provided with a threaded aperture into which an externally threaded socket may engage.

A further important optional feature of the invention is a shroud covering the flexure element at least. The shroud may have an aperture corresponding to the aperture in the main body for a socket. This shroud may additionally be provided with a slot which engages a screw means in the main body permitting twisting movement of the shroud with respect to the main body to cover or expose the said aperture.

Preferably the main body at least is of monel metal.

Figure 11:
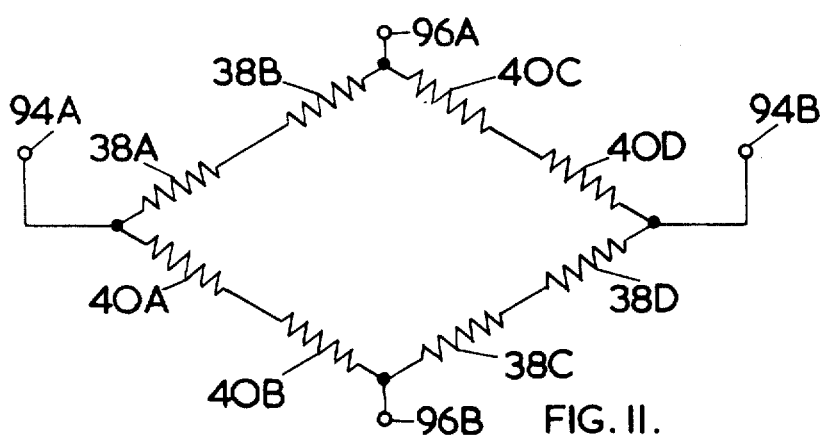
Figure 12:
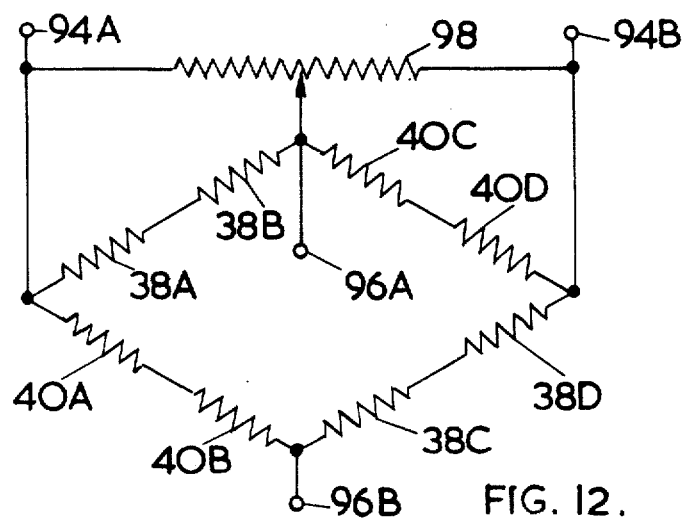

In order that the invention might be more fully understood and further features appreciated, the following description, which is by way of example only, will refer to the accompanying drawings, in which:

FIG. 1 shows an elevation of an electromechanical transducer in accordance with the present invention in partial section;

FIG. 2 is an elevation of the main body portion of the transducer of FIG. 1 in isolation, FIG. 3 is a section on the line 3–3' of FIG. 2, FIG. 4 is a section on the line 4–4' of FIG. 2, FIG. 5 is a section on the line 5–5' of FIG. 2, FIG. 6 is a section on the line 6–6' of FIG. 2, FIG. 7 shows section taken on the line 7–7' of FIG. 3, FIG. 8 shows an elevation of the end cap of the transducer of FIG. 1 in half section, FIG. 9 shows an elevation of the shroud of the transducer of FIG. 1 in half section, FIG. 10 illustrates a bridge circuit arrangement of strain gauges for use with four strain gauges on the flexure element, FIG. 11 illustrates a bridge circuit arrangement of strain gauges for use with eight strain gauges in the flexure element, FIG. 12 illustrates an improved bridge circuit for use with eight strain gauges on the flexure element, and FIG. 13 illustrates a halo-pelvic traction equipment employing the invention.

In FIGS. 1–9 an electromechanical transducer includes a main body 10 disposed about a central longitudinal axis having two end portions 30 and 31 and a flexure element 34 having two parallel plane faces 34A, 34B (FIGS. 5 and 6) separated by a rim 34C (FIG. 3) and having a central aperture 33. The flexure element 34 is disposed intermediately of the two end portions 30, 31 in a plane normal to the central axis. The flexure element 34 is joined to the end portion 30 of main body 10 by a pair of diametrically opposed pillars 32 extending in a direction parallel to the central axis of the main body from face 34A. Similarly the flexure element 34 is joined to the other end portion 31 of main body 10 by diametrically opposed pillars 36 extending in a direction parallel to the central axis of the main body from face 34B. The pillars 32 and 36 are in mutually orthogonal diameters of the flexure element 34 and adjacent the rim 34C. A central substantially square aperture 33 is provided in the flexure element (see FIGS. 5 and 6), and the rim 34C of the flexure element 34 is parallel to the edge of the aperture 33 between the pillars 32 and 36, then the flexure element is of the form of four guided cantilevers 34D between the pillars. Strain gauges are positioned in pairs on each face of the flexure element, over and under either two opposed or four opposed cantilevers at a point midway between the root and point of inflexion (i.e., the strain sensing position for calculation purposes is 1/4). Four strain gauges 38A, 38C, 40A, 40C, may be used in two pairs or eight gauges 38A–D, 40A–D, may be used in four pairs. Wires from the strain gauges 40A–D pass through holes 35 in the flexure element.

Further details of the main body 10 are best appreciated by reference to FIGS. 2 to 7. The one end portion 30 has a taper 14 towards its extremity. The taper 14 is provided with opposed notches 22 into which a spanner or often cooperating instrument may engage. A central axial bore 11 passes through the main body. The wall of this bore 11 has threads 24 within the taper 14. The perimeter of end portion 30 has a circumferential groove 26 into which an O-ring 28 (FIG. 1) engages. Two opposed radial apertures 16 and 20 are provided in the main body 10. The smaller aperture 16 is internally screw threaded. Parallel to the aperture 16 a further smaller diameter screw threaded bore 29 extends through the main body 10 from the external surface to the axial bore 11. The other end portion 31 of main body 10 has external screw threads 12 towards its extremity 13. Internally in this end portion 31 the axial bore is stepped and has a increased diameter portion 25 into which a ball bushing 58 (FIG. 1) is received.

As will be appreciated from FIG. 11 the screw threads 12 engage internal threads 46 of an end cap 42. The end cap 42 has a countersunk aperture 52 through which screw 72 passes engaging a threaded bore 15 in main body 10 to lock the end cap 42 in position. The end cap has a central bore 44 passing through, which bore is expanded in steps 56 and 54 to increased diameter. The cap has a taper 48 whose surface has notches 49 for the engagement of a spanner or other cooperating instrument. Internally of the taper 48 the bore 44 has threads 50. Detail of the end cap is best decerned in FIG. 8.

The ball bushing 58 is retained within the increased diameter portion 25 of bore 11 both by a circular clip 60 having lugs trapped between extremity 13 of the main body 10 and step 54 and by engagement of step 56. Extending through part of the bore 11 and aperture 33 of the flexure element is a rod 62 closely fitting within bore 11 to restrict lateral deflection of the transducer.

External electrical connection to the transducer may be made by a multi-pin plug engaging a multi-pin socket 18 externally threaded to engage the threads of aperture 16 of the main body 10. The large diameter aperture 20 will be seen in FIG. 1 to permit access to the rear of the socket 18. From the socket internal wiring passes through bore 41 parallel to the central longitudinal axis in main body 10 to a multi-way tag strip 37 (FIG. 4) mounted in a recess the end 30 of the main body. From the tag strip individual connections are made to the strain gauges 38A–D, 40A–D, the connections passing through holes 35 in the flexure element 34 as appropriate. To partially protect the wires and the strain gauges their exposed parts are covered with a padding compound.

A shroud 64, a tight sliding fit over O-ring 28 is provided, to protect the strain gauges and internal wiring of the main body. The shroud is shown in detail in FIG. 9. It has an aperture 66 (substantially the same diameter as aperture 16 of main body 10) and a slot 68 extending around a part of the perimeter of the shroud. A knurl 70 is provided to facilitate twisting of the shroud.

In FIG. 1 it will be seen that a screw 74 passes through the slot 68 to engage threaded bore 29 of the main body 10. This permits the shroud 64 to be rotated with respect to the main body 10 exposing aperture 16 to permit entry of a plug to socket 18 to take load measurements. When the plug is removed the shroud is turned again closing the aperture 16.

Further protection to the transducer is given by screw threaded plugs 76 and 80 engaging threads 24 and 44 respectively (FIG. 1). These plugs are provided with slots 78 and 82 respectively for the engagement of a screwdriver or like cooperating means to adjust their position. These plugs serve to prevent foreign bodies being forced into the interior of the transducer, and, in particular, over insertion of the rods 86 and 90 whose stress the transducer is to measure. Additionally the plug 80 also serves to adjust, to some small extent, the amount of movement permitted by the internal rod 62.

The rods 86 and 90, for example, rods of halo-pelvic traction equipment have threaded ends to engage the threads 24 and 44. Lock nuts 88 and 92 are provided to lock the rods in position.

It will be appreciated that the rods 86 and 90 and locknuts 88 and 92 form no part of the present invention.

In FIG. 10 illustrating a four strain gauge system; the strain gauges are arranged in two opposed pairs 38A/40A & 38C/40C, one each pair (38A, 38C) on face 34A of flexure element 34 (see FIG. 5) the other of each pair (40A, 40C) on face 34B of flexure element 34 (see FIG. 6). The strain gauges 38A and 38C are arranged on opposed arms of the bridge, as are the strain gauges 40A and 40C. A voltage is applied between the terminals 94A and 94B and the out of balance due to a load applied along the longitudinal axis of the transducer measured between the terminals 96A and 96B of the bridge.

One of the problems with a four gauge system is that small errors may occur in the measurement of tensile loads due to a small amount of bend of the transducer occurring. This is eliminated as far as possible by the rod 62, however to be absolutely certain of avoiding any errors from this source an eight gauge network is used (FIG. 11). The position of the gauges 38A-D, 40A-D, on the surfaces of the flexure element can be seen by reference to FIGS. 5 and 6. The circuit shown in FIG. 11 requires that the strain gauges be in matched pairs, to overcome this requirement a potentiometer 98 (FIG. 12) may be included to adjust the bridge to "zero" output before application of a load.

FIG. 13 illustrates the application of the invention to a halo-pelvic traction equipment. The equipment comprises a framework comprising four lower rods 102 and four corresponding upper cranked rods 106. The lower rods 102 are each linked to the upper rods 106 by transducers 100 in accordance with the invention. Locking nuts 104 and 108 are illustrated retaining the rods in position in transducer. The upper rods 106 are each bolted by bolts 112 to skull ring 110. Adjusting screws 114 are provided in the skull ring 110 to firmly engage the skull of a patient. The lower bars 102 are provided with threads 118 towards their end and are bolted to a hip ring 116 by adjusting bolts 120. A pair of hip bars 122 are provided engaging the hips and bolted to the hip ring 116 by bolts 124.

In operation the shroud (64 in FIG. 1) and transducer 100 is twisted to expose its socket (18 in FIG. 1). Into the socket a plug is inserted to connect the strain gauges on the flexure element to a meter (e.g. a galvanometer). Adjusting bolts 120 are then adjusted against hip ring 116 until the requisite load is registered on the meter. The plug is removed from the socket and the shroud twisted to cover the socket, screw 74 (FIG. 11) being tightened to prevent accidental movement of the shroud 64 (FIG. 1). Adjustments are made to the loads in all bars in a similar way. After the load is applied the patient is then free to move around until another adjustment of the load is required which is carried out in a similar manner.

It will be appreciated that the application of the transducer of the invention to halo-pelvic traction as discussed with reference to FIG. 13 is merely examplary of one of the principal uses of the invention and should in no way be considered limiting upon the invention as defined in the applicant's several claims, except insofar as any claim claims the transducer in connection with a halo-pelvic traction equipment. This invention will find application in many arts where a comparitively lightweight and very sensitive electromechanical transducer is required.

In the particular application described the transducer parts were machined from stress relieved monel metal. This alloy produces good sensitivity, is easy to gauge, and size for size has a greater rigidity in the unwanted planes a diaphragm or cantilever beam. The weight of the transducer can be reduced by making the shroud and the cap of aluminium or aluminium alloy.

The strain gauges are conveniently of the linear foil type, 120 ohms, compensated for apparent strain and have a zero gauge factor variation over a very wide range of ambient temperature.

I claim:

1. An electro-mechanical transducer including a substantially cylindrical main body disposed about a longitudinal central axis, said main body including:
   two end portions, each of said end portions having a longitudinal axial bore extending at least part way therethrough,
   a flexure element disposed in a plane normal to said central axis, said flexure element having a pair of mutually parallel surfaces connected by a rim,
   at least one strain gauge mounted on said parallel surfaces of said flexure element,
   at least one first pillar extending in a direction parallel to the longitudinal central axis of the main body and connecting said flexure element with one of said end portions,
   at least one second pillar extending in a direction parallel to the longitudinal central axis of the main body and connecting said flexure element with the other of said end portions, and
   a rod located in said bore to reduce bending of said transducer.

2. An electro-mechanical transducer according to claim 1, wherein the flexure element comprises a plurality of guided cantilevers.

3. An electro-mechanical transducer according to claim 1, including a ball bushing in which said rod is journalled.

4. An electro-mechanical transducer according to claim 3, including screw threads towards either end of said bore and screw threaded plugs engaging said screw threads.

5. An electro-mechanical transducer according to claim 4, wherein threads of bars of a halo-pelvic traction equipment engaged said screw threads.

6. An electro-mechanical transducer according to claim 3, including an end cap, said end cap bearing against said ball bushing to retain said ball bushing in place.

7. An electro-mechanical transducer according to claim 1, including an end cap.

8. An electro-mechanical transducer according to claim 1, additionally including a screw means protruding from said main body, an aperture in said main body, said aperture being threaded to receive the external threads of an externally threaded socket, and a shroud, said shroud having an aperture and a slot, said slot engaging said screw means in said main body to permit rotational movement of said shroud with respect to said main body and to bring said aperture in said shroud into coincidence with said aperture in said main body.

9. An electro-mechanical transducer according to claim 1, wherein at least said main body comprises monel metal.

10. An electro-mechanical transducer including a substantially cylindrical main body disposed about a longitudinal central axis, said main body including:
- two end portions, each of said end portions having a longitudinal axial bore extending at least part way therethrough,
- a flexure element disposed in a plane normal to said central axis, said flexure element having a pair of mutually parallel surfaces connected by a rim,
- at least two pairs of strain gauges, a first strain gauge of each pair being mounted on one of said parallel surfaces of said flexure element, the second strain gauge of each of said pairs being mounted on the other of said parallel surfaces of said flexure element, each of said second strain gauges being opposite said first strain gauge of its pair,
- a pair of diametrically opposed first pillars extending from one surface of the flexure element in a direction parallel to the longitudinal central axis of the main body and connecting said flexure element with one of said end portions,
- a pair of diametrically opposed second pillars extending from the other surface of the flexure element in a direction parallel to the longitudinal central axis of the main body and connecting said flexure element with the other of said end portions, said second pillars being disposed orthogonally of said first pillars, and
- a rod located in said bore to reduce bending of the transducer.

11. An electro-mechanical transducer according to claim 10 wherein said flexure element comprises four guided cantilevers.

12. An electro-mechanical transducer according to claim 11 having four pairs of strain gauges arranged as opposed pairs on the parallel surfaces of said flexure element, with one pair on each of said guided cantilevers.

13. An electro-mechanical transducer according to claim 12, wherein said strain gauges are mounted at a point midway between the root and the point of inflection of each of said guided cantilevers.

14. An electro-mechanical transducer according to claim 10, including a ball bushing in which said rod is journalled.

15. An electro-mechanical transducer according to claim 14, including screw threads towards either end of said bore and screw threaded plugs engaging said screw threads.

16. An electro-mechanical transducer according to claim 15, wherein threads of bars of a halo-pelvic traction equipment engage said screw threads.

17. An electro-mechanical transducer according to claim 14, including an end cap, said end cap bearing against said ball bushing to retain said ball bushing in place.

18. An electro-mechanical transducer according to claim 10, including an end cap.

19. An electro-mechanical transducer according to claim 10, additionally including a screw means protruding from said main body, an aperture in said main body, said aperture being threaded to receive the external threads of an externally threaded socket, and a shroud, said shroud having an aperture and a slot, said slot engaging said screw means in said main body to permit rotational movement of said shroud with respect to said main body and to bring said aperture in said shroud into coincidence with said aperture in said main body.

20. An electro-mechanical transducer according to claim 10, wherein at least said main body comprises monel metal.

21. An electro-mechanical transducer comprising a main body disposed about a longitudinal central axis, said main body including:
- two end portions,
- a flexure element disposed in a plane normal to said central axis, said flexure element having a pair of mutually parallel surfaces connected by a rim,
- a pair of diametrically opposed first pillars extending from one surface of said flexure element in a direction parallel to the longitudinal central axis of the main body and connecting said flexure element with one of said end portions,
- a pair of diametrically opposed second pillars extending from the other surface of said flexure element in a direction parallel to the longitudinal central axis of said main body and connecting said flexure element with the other of said end portions, said second pillars being disposed orthogonally of said first pillars,
- at least four pairs of strain gauges, the first strain gauge of each pair being mounted on one of said parallel surfaces of said flexure element, the second strain gauge of each pair being mounted on the other of said parallel surfaces of said flexure element with each of said second strain gauges opposite said first strain gauge of its pair, said flexure element comprising four guided cantilevers with said strain gauges mounted at a point midway between the root and the point of inflection of each of said guided cantilevers, the electro-mechanical transducer additionally having a longitudinal axial bore,
- a rod retained in said bore and journalled in a ball bushing,
- an end cap,
- said end cap engaging said ball bushing,
- screw threads towards either end of said axial bore and screw threaded plugs engaging said screw threads,
- a screw means protruding from said main body,
- an aperture in said main body, said aperture being threaded to receive the external threads of an externally threaded socket,
- a shroud, said shroud having an aperture and a slot, said slot engaging said screw means in said main body to permit rotational movement of said shroud with respect to said main body and to bring said aperture in said shroud into coincidence with said aperture in said main body,
- said main body being of monel nickel.

22. An electro-mechanical transducer according to claim 1, wherein threads of bars of a halo-pelvic traction equipment engage said screw threads towards either end of said axial bore.

* * * * *